(12) United States Patent
Quiroz-Mercado et al.

(10) Patent No.: US 7,354,416 B2
(45) Date of Patent: Apr. 8, 2008

(54) METHODS AND DEVICES FOR DRAINING FLUIDS AND LOWERING INTRAOCULAR PRESSURE

(76) Inventors: Hugo Quiroz-Mercado, Oftalmologia Media Sur, Puenta de Piedra, 150-514, Mexico, D.F. (MX) 14050; Hampar L. Karageozian, 31021 Marbella Vista, San Juan Capistrano, CA (US) 92673

( * ) Notice: Subject to any disclaimer, the term of this patent is extended or adjusted under 35 U.S.C. 154(b) by 237 days.

(21) Appl. No.: 10/781,343

(22) Filed: Feb. 18, 2004

(65) Prior Publication Data
US 2004/0254517 A1    Dec. 16, 2004

Related U.S. Application Data

(60) Provisional application No. 60/447,999, filed on Feb. 18, 2003.

(51) Int. Cl.
*A61M 5/00* (2006.01)
*A61B 17/08* (2006.01)

(52) U.S. Cl. ............................ 604/8; 604/264; 606/153

(58) Field of Classification Search ............... 604/8, 604/9, 264; 606/4, 6, 107, 108, 153; 623/6.12; 424/94.62
See application file for complete search history.

(56) References Cited

U.S. PATENT DOCUMENTS

| | | | |
|---|---|---|---|
| 3,788,327 A * | 1/1974 | Donowitz et al. | 604/247 |
| 4,402,681 A * | 9/1983 | Haas et al. | 604/9 |
| 4,490,351 A * | 12/1984 | Clark, Jr. | 424/9.4 |
| 5,171,231 A * | 12/1992 | Heiliger | 604/263 |
| 5,266,580 A | 11/1993 | Chiou | |
| 5,300,020 A | 4/1994 | L'Esperance, Jr. | |
| 5,326,345 A | 7/1994 | Price, Jr. | |
| 5,626,559 A | 5/1997 | Solomon | |
| 6,306,114 B1 | 10/2001 | Freeman et al. | |
| 6,610,292 B2 * | 8/2003 | Karageozian et al. | 424/94.62 |
| 6,863,073 B2 * | 3/2005 | D'Amico et al. | 128/898 |

* cited by examiner

*Primary Examiner*—Leslie R. Deak
(74) *Attorney, Agent, or Firm*—Robert D. Buyan; Stout, Uxa, Buyan & Mullins, LLP

(57) ABSTRACT

Methods, devices and systems for draining fluid from the eye and/or for reducing intraocular pressure. A passageway (e.g., an opening, puncture or incision) is formed in the lamina cribosa or elsewhere to facilitate flow of fluid from the posterior chamber of the eye to either a) a subdural location within the optic nerve or b) a location within the subarachnoid space adjacent to the optic nerve. Fluid from the posterior chamber then drains into the optic nerve or directly into the subarachnoid space, where it becomes mixed with cerebrospinal fluid. In some cases, a tubular member (e.g., a shunt or stent) may be implanted in the passageway. A particular shunt device and shunt-introducer system is provided for such purpose. A vitrectomy or vitreous liquefaction procedure may be performed to remove some or all of the vitreous body, thereby facilitating creation of the passageway and/or placement of the tubular member as well as establishing a route for subsequent drainage of aqueous humor from the anterior chamber, though the posterior chamber and outwardly though the passageway where it becomes mixed with cerebrospinal fluid.

18 Claims, 5 Drawing Sheets

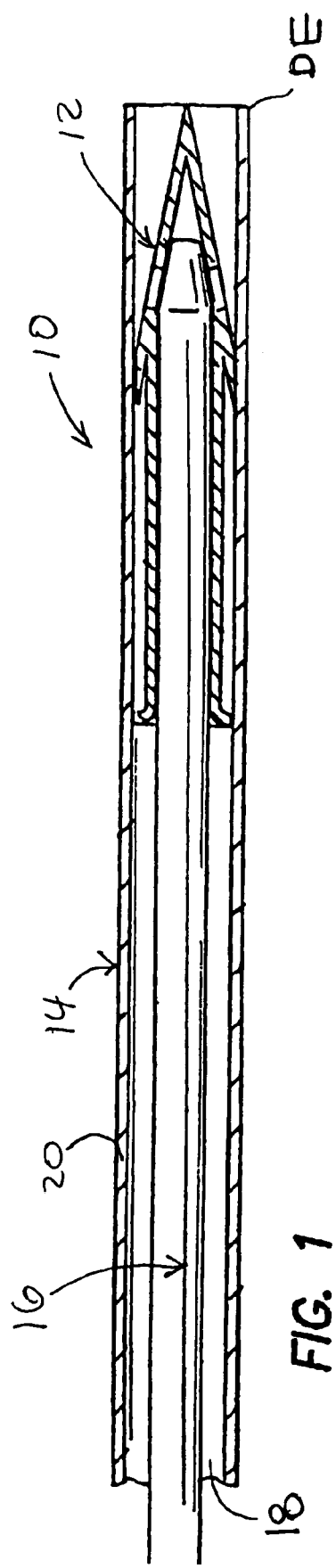
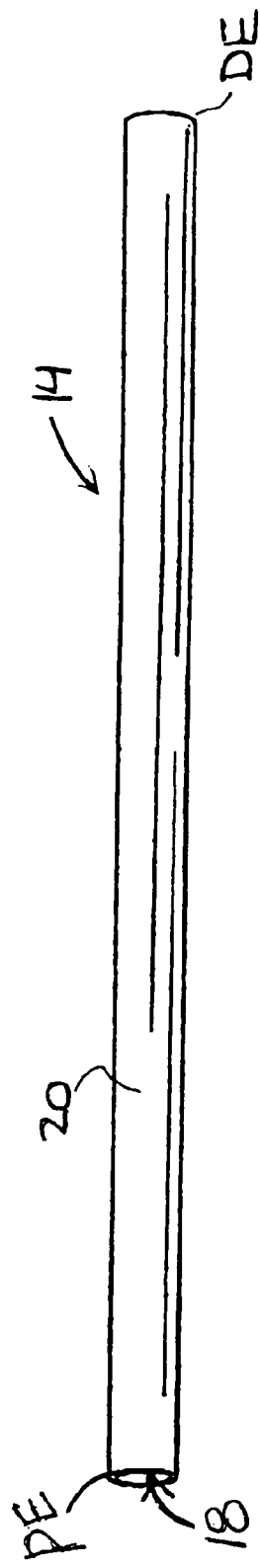
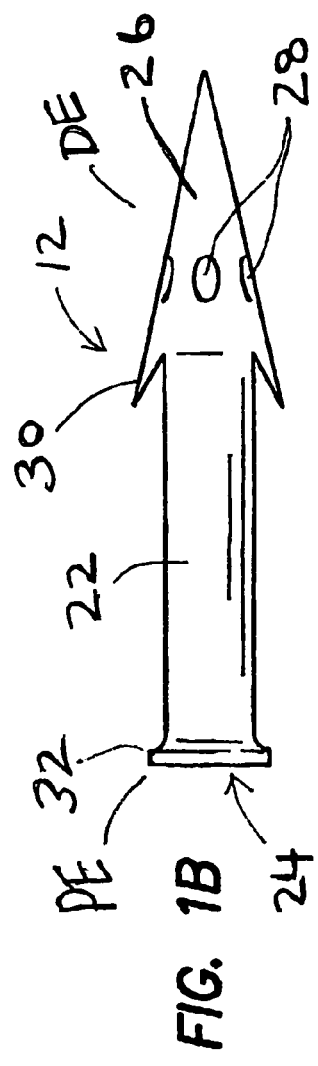
FIG. 1
FIG. 1A
FIG. 1B

METHODS AND DEVICES FOR DRAINING FLUIDS AND LOWERING INTRAOCULAR PRESSURE

RELATED APPLICATION

This application claims priority to U.S. Provisional Patent Application No. 60/447,999 filed on Feb. 18, 2003, the entirety of which is expressly incorporated herein by reference.

FIELD OF THE INVENTION

This invention relates generally to medicine and surgery, and more particularly to methods and devices for lowering intraocular pressure in human or veterinary patients.

BACKGROUND OF THE INVENTION

In normal adults the ocular globe is approximately spherical, with a diameter averaging 24.5 mm. The cornea is a transparent tissue inserted into the sclera at the limbus, the anterior chamber is behind the cornea. The iris is the anterior extension of the ciliary body, it presents as a flat surface with a centrally situated round aperture, the pupil. The iris lies in contiguity with the anterior surface of the lens, dividing the anterior chamber from the posterior chamber, each of which contains aqueous humor. The lens is a biconvex, avascular, colorless and almost completely transparent structure about 4 mm thick and 9 mm in diameter. The lens is suspended behind the iris by the zonules, which connect it with the ciliary body. Anterior to the lens is the aqueous humor and posterior to the lens is the vitreous. The "vitreous body" which occupies approximately four fifths of the cavity of the eyeball, behind the lens. The vitreous body is formed of gelatinous material, known as the vitreous humor. Typically, the vitreous humor of a normal human eye contains approximately 99% water along with 1% macromolecules including: collagen, hyaluronic acid, soluble glycoproteins, sugars and other low molecular weight metabolites.

The retina is essentially a layer of nervous tissue formed on the inner posterior surface of the eyeball. The retina is surrounded by a layer of cells known as the choroid layer. The retina may be divided into a) an optic portion which participates in the visual mechanism and b) a non-optic portion which does not participate in the visual mechanism. The optic portion of the retina contains the rods and cones, which are the effectual organs of vision. A number of arteries and veins enter the retina at its center, and splay outwardly to provide blood circulation to the retina. The posterior portion of the vitreous body is in direct contact with the retina. Networks of fibrillar strands extend from the retina and permeate or insert into the vitreous body so as to attach the vitreous body to the retina.

The optic nerve provides communication between the retina and the brain. The optic nerve is primarily composed of axons from the retinal ganglion cells along with glial support cells and other tissue. The optic nerve begins at the optic nerve head or disc and passes through the sclera in the area of the lamina cribrosa. The optic nerve then passes through the orbit and optic canal to the optic chiasm. Posterior to the lamina cribrosa, the optic nerve is surrounded by a three-layered meningeal sheath similar to the central nervous system which consists of a dura mater (optic nerve sheath), arachnoid mater, and pia mater. The subarachnoid space surrounding the optic nerve is in direct communication with the subarachnoid space of the central nervous system.

The term "glaucoma" encompasses a group of diseases that cause progressive damage to the optic nerve and resultant optical field defects, vision loss and, in some cases, blindness. Glaucoma is typically, but not always, accompanied by abnormally high intraocular pressure. There are three basic types of glaucoma—primary, secondary and congenital. The primary type of glaucoma is most common. Cases of primary glaucoma are classified as either open angle or closed angle. Secondary glaucoma occurs as a complication of a variety of other conditions, such as injury, inflammation, vascular disease and diabetes. Congenital glaucoma is elevated eye pressure present at birth due to a developmental defect in the eye's drainage mechanism.

As well as being an important marker of the presence and advancement of glaucoma, the structure of the optic nerve head may play a role in the pathogenesis of glaucoma. Two main theories exist for the mechanism of optic nerve damage in glaucoma. One theory, known as the mechanical IOP related theory, suggests that the pressure head acts directly on the lamina cribosa. The lamina cribosa is not well supported superiorly and inferiorly at the disk and, as a result, initial damage occurs superiorly and inferiorly to produce the characteristic arcuate defects. Variations in the ganglion cell support at the disk may explain the variations between IOP susceptibilities of individuals with similar IOP's. The second theory, known as the vascular mechanism of damage theory, suggests that changes occur within the microcirculation of the disk capillaries and such microvascular changes are responsible for glaucomatous changes.

Irrespective of the type of glaucoma a patient suffers from, controlling IOP through the use of drugs and/or surgery is a mainstay of treatment. It is generally acknowledged that lowering intraocular pressure in glaucoma patients can prevent or lessen the irreversible glaucoma-associated destruction of optic nerve fibers and the resultant irreversible vision loss.

Presently the use of topically applied glaucoma medications consisting of mainly beta blockers, prostaglandin analogues, alpha-2 agonists, and carbonic anhydrase inhibitors are short acting, prone to deleterious side effects, prone to compliance issues, and must be used for life. Also, at present, the use of argon laser trabeculoplasty as a means for treating glaucoma is limited in clinical response, lasts only approximately 1-2 years, and is limited by the number of applications per eye. Also, at present, the performance of trabeculectomy procedures with or without antimetabolites allows for the external drainage of aqueous humor from the eye. However, trabeculectomy procedures can be technically difficult, frought with early hypotony, late failure, and high rate of endophthalmitis leading to permanent loss of the eye.

Another surgical approach to the treatment of glaucoma involves the implantation of a shunt to drain aqueous humor from the anterior chamber of the eye. Examples of glaucoma shunts of the prior art include those described in the following U.S. Pat. No. 5,626,558 entitled "Adjustable Flow Rate Glaucoma Shunt and Method of Using Same;" U.S. Pat. No. 6,007,510 entitled "Implantable Devices and Methods for Controlling the Flow of Fluids Within the Body;" U.S. Pat. No. 6,007,511 entitled "Shunt Valve and Therapeutic Delivery System for Treatment of Glaucoma and Methods and Apparatus for its Installation;" U.S. Pat. No. 6,142,969 entitled "Sutureless Implantable Device and Method for Treatment of Glaucoma" and U.S. Pat. No. 6,626,858 entitled "Shunt Device and Method for Treating Glaucoma." The entire disclosure of each of these United States patents is expressly incorporated herin by reference.

Thus, there remains a need in the art for the development of new methods and apparatus for lowering IOP and/or for draining fluid from the posterior chamber of the eye for treatment of glaucoma or other disease states.

SUMMARY OF THE INVENTION

The present invention provides devices and methods for draining fluid from the posterior chamber of the eye into the optic nerve and/or the subarachnoid space. The posterior chamber of the eye is in direct fluidic communication with the anterior chamber of the eye. Thus, the methods and devices of the present invention may be used to treat diseases that are characterized by excess production and/or impaired drainage of aqueous humor (e.g., glaucoma) as well as other vitreoretinal disease states (e.g., for clearance of vitreous hemorrhage).

In accordance with the invention, there is provided a method for draining fluid from the posterior chamber of the eye by creating a passageway between the posterior chamber of the eye and either i) a location within the optic nerve or ii) a location within the subarachnoid space. Contiguous communication between the anterior chamber, posterior chamber and subarachnoid space may be achieved by additionally performing either a) complete or partial surgical removal of the vitreous humor (e.g., a vitrectomy) or b) liquefaction of all or a portion of the vitreous humor (e.g., pharmacologic vitreolysis by intravitreal administration of urea; a urea derivative; a compound having a urea group; hyaluronidase or any other enzyme or agent that causes vitreal liquefaction). The passageway by which the fluid drains from the posterior chamber into the subarachnoid space may simply comprise a hole or puncture made in the lamina cribosa or other suitable location. Alternatively, the passageway may comprise a tubular shunt device that is implanted so as to drain fluid from the posterior chamber into the optic nerve or into the subarachnoid space. Fluid which first drains into the optic nerve will diffuse into the subarachnoid space where it becomes mixed with CSF. Fluid which drains directly into the subarachnoid space will mix with CSF within the subarachnoid space. In applications of the method wherein a shunt device is employed, the shunt device may alternatively extend between the anterior chamber and subarachnoid space such that it bypasses the posterior chamber or vitreous cavity (i.e., the shunt device may extend through a subconjunctival or subscleral tunnel), furthermore the shunting device may also incorporate a system of communication between the anterior chamber and subarachnoid space that bypasses the vitreous humor by passing directly through it (e.g., a tube that extends through the vitreous body).

Further in accordance with the invention, there is provided a shunt device for draining fluid from the posterior chamber of the eye into the optic nerve or subarachnoid space. Such shunt device comprises a tube having a proximal end, a distal end and a lumen extending longitudinally therethrough, a substantially tissue penetrating tip on the distal end of the tube, a plurality of openings formed at or near the distal end of the tube to allow fluid to drain out of the lumen of the tube and at least one tissue engaging member configured to allow the shunt device to be advanced, tip member first, into tissue but to engage said tissue in such a manner as to subsequently deter retraction of the shunt out of the tissue. Optionally, the shunt device may additionally include a pressure control and/or one-way valve to control the magnitude of the pressure head required to cause fluid to drain from the eye through the shunt device and/or to prevent unwanted backflow of fluid into the eye through the shunt device. Also, optionally, the shunt device may comprise a shielding member, such as a semi-permeable membrane, to prevent or deter clogging of the shunt device by foreign matter and or tissue in-growth.

Still further in accordance with the present invention, there is provided a system that comprises a shunt device of the above-described character in combination with an introducer that is insertable into the eye and useable to implant the shunt device at its desired implantation position within or adjacent to the optic nerve. Such introducer may comprise a tubular cannula through which the shunt device may be passed and/or an elongate member which may be used to drive or advance the shunt device to its intended location. In some embodiments, the elongate member may be used without the tubular cannula. In other applications, the shunt device will be initially loaded into the lumen of the tubular cannula and the elongate member (e.g., a solid or tubular pusher rod) may be used to push the shunt device out of the distal end of the cannula and to its intended site of implantation.

Further aspects and elements of the present invention will become apparent to those of skill in the relevant art upon reading and considering the following detailed description and the accompanying drawings to which it refers.

BRIEF DESCRIPTION OF THE DRAWINGS

FIG. 1 is a longitudinal sectional view of one embodiment of an ocular shunt implantation system of the present invention.

FIG. 1A is a perspective view of the cannula component of the ocular shunt implantation assembly of FIG. 1.

FIG. 1B' is a partial cut-away/sectional view of a shunt device of the present invention incorporating an optional one-way valve to deter backflow and optional shielding member (e.g., a semi-permeable membrane) to deter clogging of the shunt due to debris or cellular tissue ingrowth.

DETAILED DESCRIPTION OF THE PREFERRED EMBODIMENT

The following detailed description and the accompanying drawings are provided for the purpose of describing certain non-limiting examples or embodiments of the invention only. This detailed description is not intended to describe all possible examples and embodiments of the invention and, thus, shall not limit the scope of the claimed invention in any way.

Figure 1B:
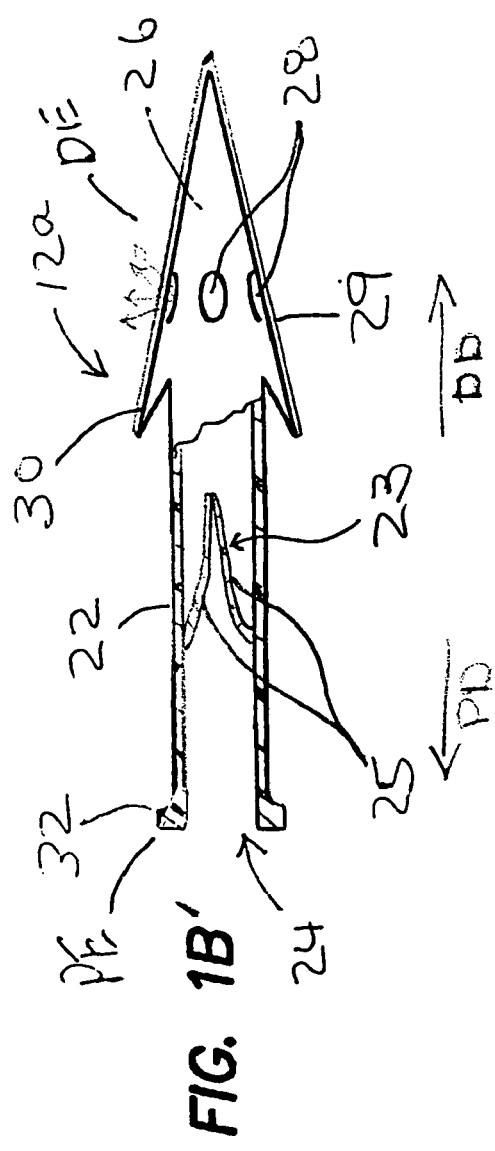
FIG. 1B is a perspective view of the shunt component of the ocular shunt implantation assembly of FIG. 1.
Figure 1C:
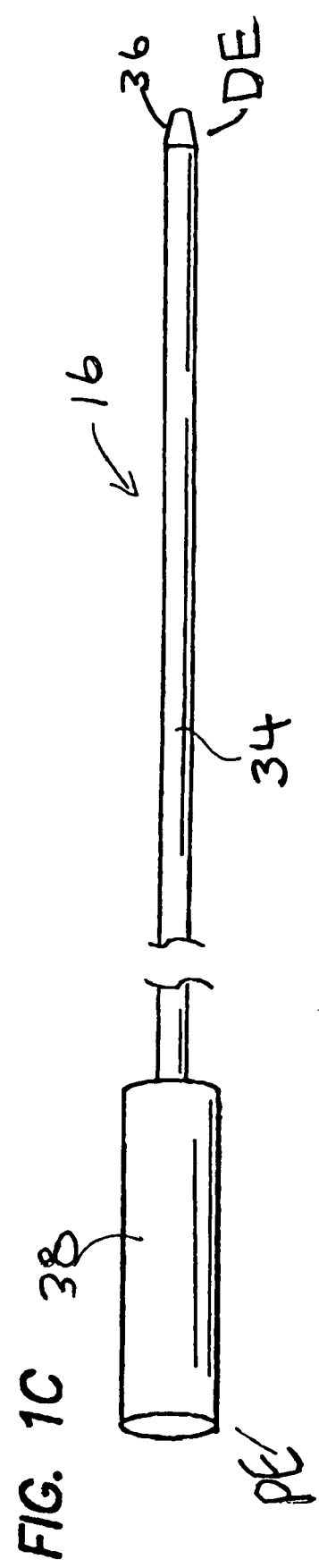
FIG. 1C a perspective view of the pusher component of the shunt implantation assembly of FIG. 1.
Figure 2A:
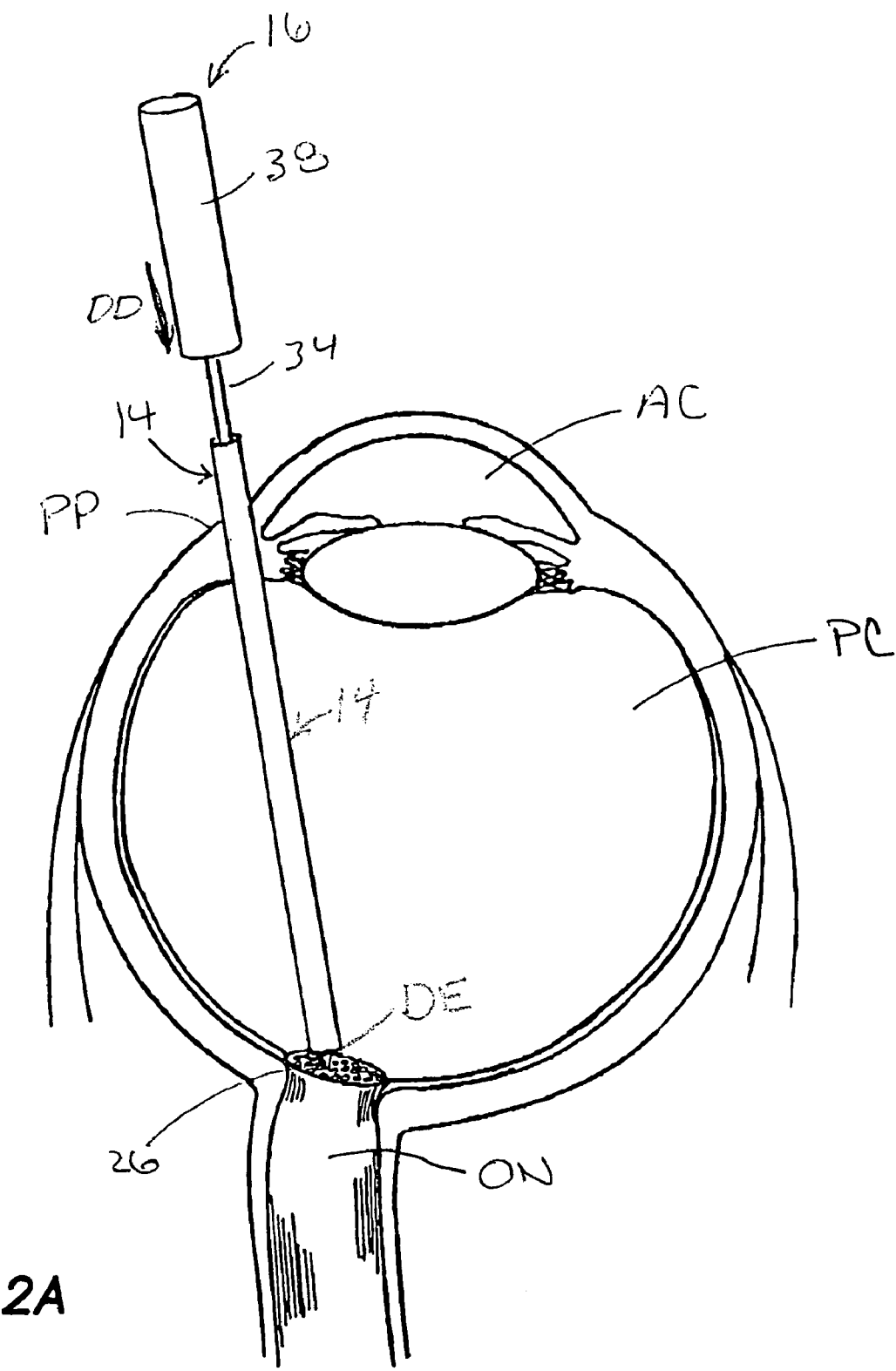
FIG. 2A is a cross-sectional view of a human eye into which an ocular shunt implantation system of the present invention has been inserted and positioned for advancement/implantation of the shunt.

FIGS. 1-1C show one embodiment of a system 10 for implantation of a shunt device 12 in accordance with the present invention. This system 10 generally comprises the shunt device 12, a cannula 14, and a pusher 16. As shown in FIG. 1, the shunt device 12 is initially positioned within the lumen 18 of the cannula 14 and the pusher 16 is positioned in the lumen 18 of the cannula 14 behind the shunt device 12 such that the pusher 16 may be used to push the shunt device 12 out of the distal end DE of the of the cannula 14. One way of performing this shunt-expulsion procedure is shown in FIG. 2A and is explained in detail hereblow.

The particular embodiment of the shunt 12 shown in FIG. 1B comprises a tube 22 having a lumen 24 extending longitudinally therethrough. A tip member 26 is positioned on the distal end of the tube 22. The tip member 26 of this embodiment is generally conical in shape, but it will be understood that the tip member may be beveled, tapered, trocar tipped or of any other shape that will allow it to advance through tissue as explained herebelow. Apertures 28 are formed in the side wall of the tip member 26 to allow fluid to drain out of the lumen 24 of the tube 22. Optional tissue engaging members 30, such as barbs, hooks, undercuts, adhesive regions, tissue in-growth receiving areas, etc., may be formed on the shunt 12 to deter unwanted movement or retraction of the shunt 12 after it has been advanced to its intended implantation position. Also, optionally, a flange (e.g., any laterally extending member or area or increased diameter) may be formed on the proximal end of the tube 22 to engage the lamina cribosa or other tissue in a manner that deters advancement of the tube beyond its intended position. The shunt device 12 may have a diameter or cross-dimension at its widest point of about 1 micron to about 2000 and preferably of about 50 microns to about 400 microns.

FIG. 1B' shows an alternative embodiment of the shunt device 12a which has the same construction as the shunt device 12 shown in FIG. 1B but additionally includes an optional one way valve 23 and an optional shielding member 29 which covers the apertures 28 to prevent or deter the entry of foreign matter or issue ingrowth through apertures 28. The one way valve 23 serves to allow fluid flow in the distal direction (Arrow DD) while preventing or substantially deterring backflow in the proximal direction (Arrow PD). The one way valve may be a duckbill type valve comprising a plurality of flexible leaflets 25, as shown, or may comprise any other suitable type of check valve or one-way valve, such as a ball type check valve, a flapper, or any of the valves typically used as hemostatic valves on small medical catheters of a size similar to this shunt device 12a. Also, this one-way valve 23 may be constructed to open only when the pressure of fluid within the lumen 24 proximal to the valve 23 exceeds a predetermined maximum, thereby providing for control of the intraocular pressure and preventing the drainage of too much fluid from the eye as may result in hypotony or other untoward sequale.

The cannula 14 may comprise a tube having a generally cylindrical wall 14, a lumen 18 extending longitudinally therethrough between an open proximal end PE and an open distal end DE.

The pusher 16 may comprise a solid or tubular elongate member 34 having a proximal end PE and a distal end DE. Optionally, a handle 38 may be positioned on the proximal end of the elongate member 34. Also, optionally, the elongate member 34 may have an outer diameter that is sized to be received within the lumen 24 of the shunt device 12 and the distal end DE of the elongate member 34 may be tapered, as shown in FIG. 1C, to seat within the tapered tip member 26 of the shunt device 12.

Some or all of the components of the system 10 may be formed of silicon, polyethylene, polypropylene, polycarbonate, stainless steel or other biologically compatible materials. In the particular embodiemt shown in the figures, the shunt device 12 or 12a may be substantially formed of silicon material. The shunt device 12 or 12a may also involve an active pumping system or may incorporate a wick like system to move fluid in the required direction.

Figure 2B:
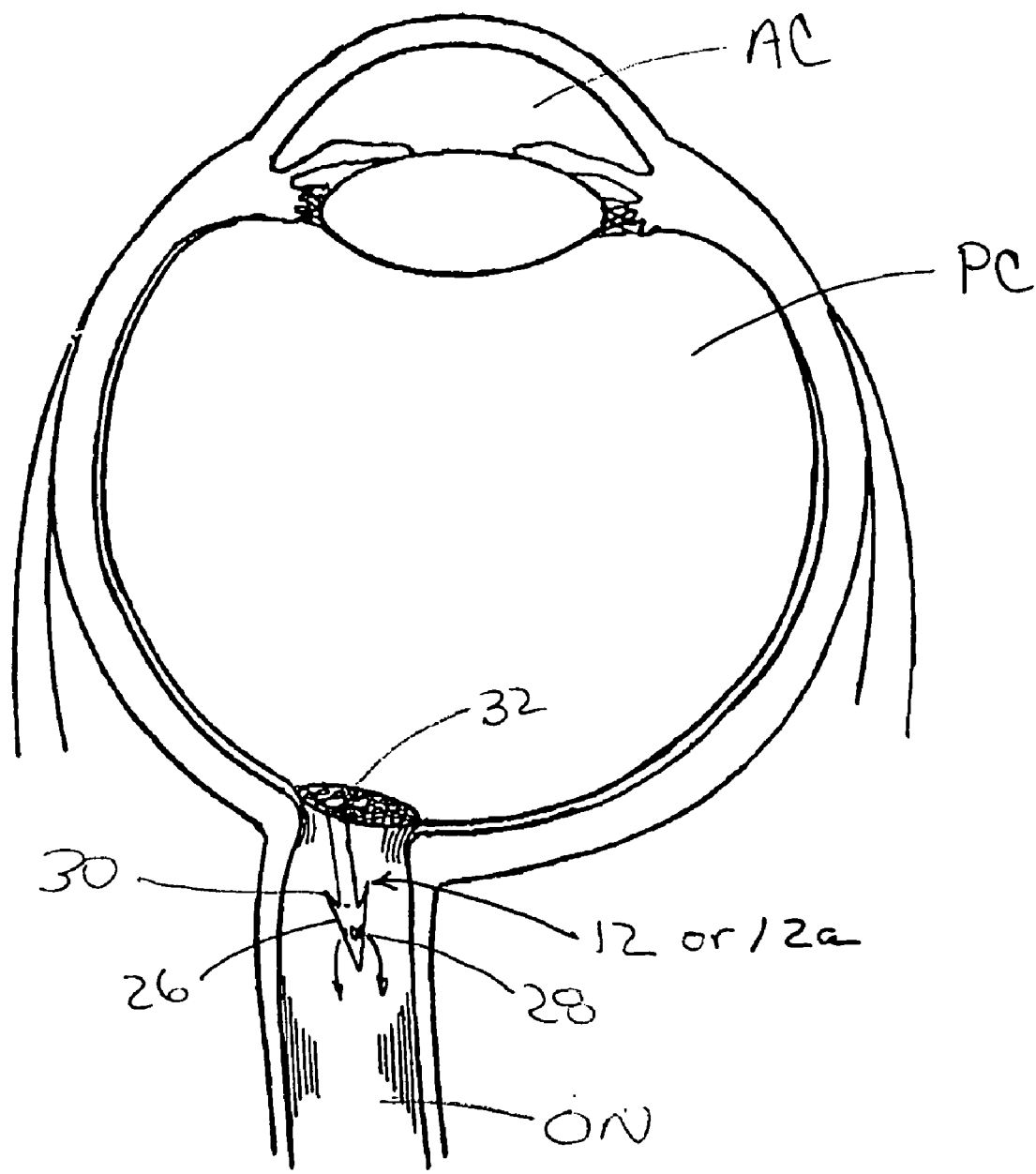
FIG. 2B is a cross-sectional view of a human eye into which an ocular shunt of the present invention has been implanted to shunt fluid from the posterior chamber of the eye into the body of the optic nerve.
Figure 2C:
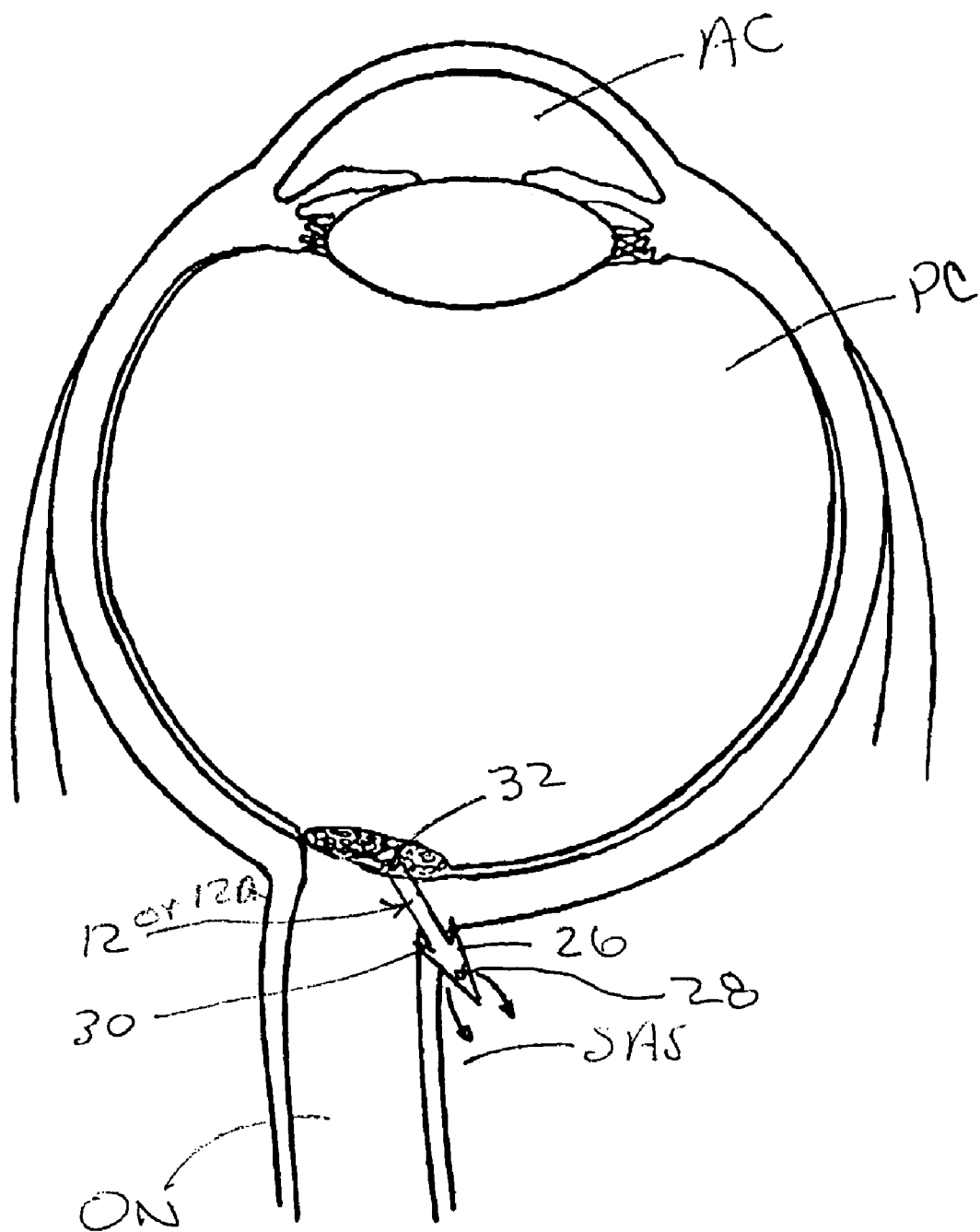
FIG. 2C is a cross-sectional view of a human eye into which an ocular shunt of the present invention has been implanted to shunt fluid from the posterior chamber of the eye into the area outside of the optic nerve.

FIG. 2A-2C show the system of FIGS. 1-1C in its currently intended mode of operation. Prior to implantation of the shunt device 12 or 12a, a vitrectomy device may be inserted into the posterior chamber PC and a vitrectomy performed to remove at least a portion of the vitreous body from the posterior chamber PC. Alternatively, all or a portion of the vitreous body may be liquefied. Such vitreal liquefaction may be accomplished by intravitreal administration (e.g., intravitreal injection) of one or more agents that cause liquefaction of the vireous humor. Examples of such agents include but are not limited to; urea, urea derivatives, compounds having urea groups, hyaluronidase and other enzymes or other substances that cause vitreal liquefaction. Descriptions of these and other substances that cause vitreal liquefaction, as well as dosage information and associated methods for administration, are found in U.S. Pat. No. 5,292,509 (Hagman): U.S. Pat. No. 6,551,590 (Karageozian et al.); U.S. Pat. No. 6,610,292 (Karageozian et al.) and U.S. Pat. No. 6,462,071 (Karageozian et al., the entireties of which are expressly incorporated herein by reference.

As shown in FIG. 2A, a small opening such as a needle puncture is made in the pars plana PP and the system 10 of the present invention is inserted through that opening and through a region of the poster chamber PC from which the vitreous body has been removed (e.g., by vitrectomy) or in which the vitreous body has been liquefied (e.g., by intravitreal injection of a vitreous liquefying agent as described above). The system 10 is advanced to position where the distal end DE of the cannula 14 is positioned immediately anterior to the lamina cribosa. The pusher 16 is then advanced in the distal direction (Arrow DD) while the cannula 14 is held stationary, thereby pushing the shunt device 12 or 12a out of the distal end DE of the cannula 14 and causing the distal tip member 26 of the shunt device 12 or 12a to penetrate through the lamina cribosa and optic nerve ON tissue. The pusher 16 is advanced until resistance is felt due to the impingement of the flange member 32 of the shunt device 12 or 12a with the optic nerve head. At this point, the shunt member 12 or 12a has been advanced to its intended implantation site and the pusher 16 and cannula 14 may be removed from the eye, leaving the shunt device 12 or 12a in place. Depending on the angle at which the shunt device 12 or 12a is advanced, its outflow apertures 28 may be positioned at a subdural location within the body of the optic nerve ON (as shown in FIG. 2B) or within the subarachnoid space adjacent to the optic nerve ON (as shown in FIG. 2C). In instances where the outflow apertures 28 are positioned within the body of the optic nerve ON (as shown in FIG. 2B), fluid that drains out of the outflow apertures 28 will subsequently diffuse and/or be transported though the optic nerve and into the subarachnoid space where it will mix with cerebrospinal fluid. In instances where the outflow apertures are located within the subarachnoid space, fluid that flows out of the outflow apertures 28 will mix with cerebrospinal fluid that resides within the subarachnoid space. In either case, the typical backpressure of fluid adjacent to the outflow apertures 28 will be low enough to facilitate drainage of excess fluid from the eye and in the distal direction (arrow DD) through the shunt device 12 or 12a.

The foregoing description is directed to certain embodiments and examples of the invention only and does not necessarily include or expressly mention each and every possible embodiment or example of the invention that is within the scope of the following claims.

What is claimed is:

1. A method for draining fluid from the posterior chamber of the eye of a human or veterinary patient, said method comprising the step of:
    A. creating a passageway between the posterior chamber of the eye and either i) a location within the optic nerve or ii) a location within the subarachnoid space, said passageway comprising an opening in the lamina cribosa.

2. A method according to claim 1 wherein Step A is carried out by implanting a tubular shunt such that fluid from the interior of the eye will enter one end of the shunt and said fluid will exit the other end of the shunt either i) at a location within the optic nerve or ii) at a location within the subarachnoid space.

3. A method according to claim 2 wherein the shunt comprises a tube having a proximal end, a distal end and least one tissue engaging member formed on the shunt to deter unwanted movement of the shunt after it has been implanted.

4. A method according to claim 3 wherein the at least one tissue engaging member comprises a barb or barb like structure that allows the shunt to be advanced through tissue in a distal direction but engages the tissue in a manner that deters subsequent retraction of the shunt in a proximal direction.

5. A method according to claim 2 wherein the shunt comprises a tube having a proximal end, a distal end and a flange member formed on the proximal end thereof.

6. A method according to claim 2 wherein the shunt comprises a tube having a valve associated therewith, said valve being operative to perform at least one valving function selected from the group consisting of a) allowing fluid to flow out of the eye but deterring fluid form backflowing into the eye and b) allowing fluid to flow out of the eye only when the fluid pressure exceeds a predetermined maximum pressure.

7. A method according to claim 2 wherein the shunt comprises a tube having a proximal end, a distal end and at least one shielding member associated therewith to deter foreing matter or cells from clogging the tube.

8. A method according to claim 7 wherein the shielding member comprises a semi-permeable membrane constructed and positioned such that fluid flowing out of the distal end of the tube will diffuse outwardly through the membrane but foreign matter and cells will not diffuse inwardly through the membrane and into the distal end of the tube.

9. A method according to claim 2 wherein the shunt comprises a tube having a distal tip that is configured to penetrate through tissue.

10. A method according to claim 2 wherein the shunt device is configured to extend through the vitreous body such that aqueous humor will drain through the shunt and into either the optic nerve or the subarachnoid space.

11. A method according to claim 1 wherein the method further comprises the performance of a vitrectomy procedure prior to, concurrently with or after the performance of Step A.

12. A method for draining fluid from the posterior chamber of the eye of a human or veterinary patient, said method comprising the step of:
    A. creating a passageway between the posterior chamber of the eye and either i) a location within the optic nerve or ii) location within the subarachnoid space;
    wherein the method further comprises liquefaction of at least a portion of the vitreous humor prior to, concurrently with or after the performance of Step A.

13. A method according to claim 12 wherein liquefaction of at least a portion of the vitreous humor is accomplished by administering to the patient a therapeutically effective amount of an agent that causes vitreal liquefaction.

14. A method according to claim 13 wherein the agent that causes vitreal liquefaction is selected from the group consisting of:
    urea;
    urea derivatives;
    compounds having urea groups;
    hyaluronidase; and
    other enzymes that cause vitreal liquefaction.

15. A method for draining fluid from the posterior chamber of the eye of a human or veterinary patient, said method comprising the step of:
    A. creating passageway between the posterior chamber of the eye and either i) a location within the optic nerve or ii) a location within the subarachnoid space by implanting a tubular shunt such that fluid from the interior of the eye will enter one end of the shunt and said fluid will exit the other end of the shunt either at a location within the optic nerve or at a location within the subarachnoid space; wherein the step of implanting the shunt comprises forming an opening in the pars plana and advancing the shunt through the pars plana opening, through the posterior chamber of the eye and into the optic nerve or lamina cribosa.

16. A method according to claim 15 wherein the shunt has a proximal opening, a distal opening and a lumen and wherein the shunt is advanced to a location where its proximal opening is positioned so as to receive fluid from the posterior chamber of the eye and its distal opening is positioned to allow said fluid to drain into the optic nerve or subarachnoid space.

17. A method for draining fluid from the posterior chamber of the eye of a human or veterinary patient, said method comprising the step of:
    A. creating a passageway between the posterior chamber of the eye and either i) a location within the optic nerve or ii) a location within the subarachnoid space by implanting a tubular shunt such that fluid from the interior of the eye will enter one end of the shunt and said fluid will exit the other end of the shunt either at a location within the optic nerve or at a location within the subarachnoid space;
    wherein the shunt is initially positioned within a cannula that has an open distal end and wherein the step of implanting the shunt comprises:
    inserting the cannula into the eye;
    positioning the distal end of the canula adjacent to the lamina cribosa;
    advancing the shunt from the cannula into the optic nerve; and
    removing the cannula while leaving the shunt implanted within the eye such that the shunt will drain fluid from the posterior chamber of the eye into either the optic nerve or the subarachnoid space.

18. A method according to claim 17 wherein a pusher is positioned in the cannula behind the shunt and wherein the step of advancing the shunt from the cannula into the optic nerve comprises advancing the pusher so as to push the shunt out of the open distal end of the cannula.

* * * * *